US00PP33161P2

(12) United States Plant Patent
Trees

(10) Patent No.: US PP33,161 P2
(45) Date of Patent: Jun. 15, 2021

(54) ***BUDDLEIA* PLANT NAMED 'SRPBUDROY'**

(50) Latin Name: ***Buddleia* hybrid**
Varietal Denomination: SRPbudroy

(71) Applicant: The Conard-Pyle Company, West Grove, PA (US)

(72) Inventor: Scott C. Trees, Arroyo Grande, CA (US)

(73) Assignee: THE CONARD PYLE COMPANY, West Grove, PA (US)

( * ) Notice: Subject to any disclaimer, the term of this patent is extended or adjusted under 35 U.S.C. 154(b) by 4 days.

(21) Appl. No.: 16/602,925

(22) Filed: Dec. 30, 2019

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02; A01H 5/00
See application file for complete search history.

(56) References Cited

U.S. PATENT DOCUMENTS

PP22,064 P2 * 8/2011 Valin ..... A01H 5/02 Plt./242
PP23,463 P2 3/2013 Valin
PP26,305 P3 * 1/2016 Dirr ..... A01H 5/02 Plt./242

* cited by examiner

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of *Buddleia* plant, herein referred to by its cultivar name, 'SRPbudroy', is provided which forms on a substantially continuous basis attractive deep purple colored flowers. Attractive, dark green colored foliage is formed. The growth habit is upright and the plant has moderate growth vigor. The new variety is well suited for providing attractive ornamentation in the landscape.

3 Drawing Sheets

Figure 1:
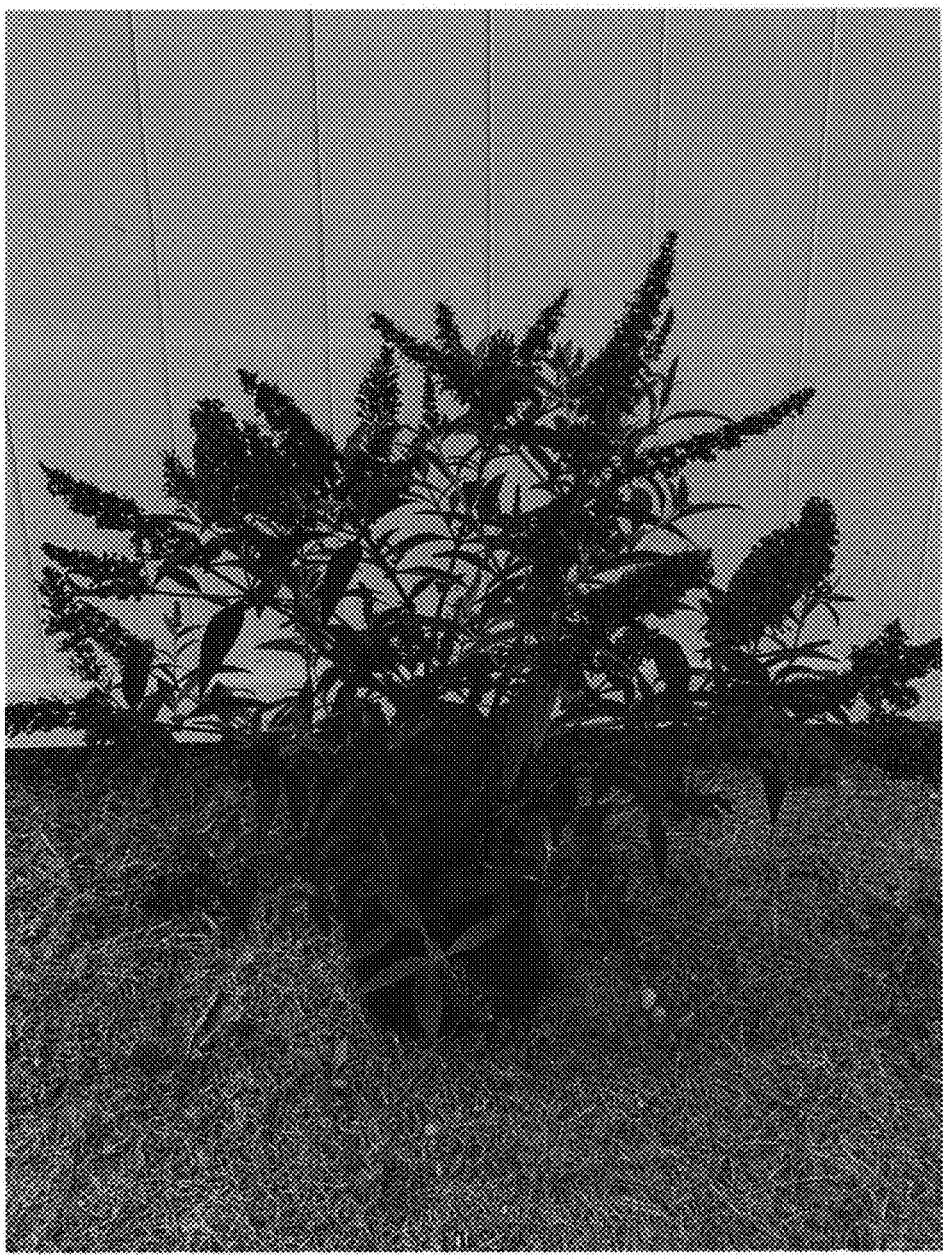

Botanical/commercial classification:
Latin name: *Buddleia* hybrid.
Varietal denomination: 'SRPbudroy'.

SUMMARY OF THE INVENTION

The new variety of *Buddleia* hybrid plant originated in a controlled breeding program in Guadalupe, Calif. during August 2013. The objective of the breeding program was the development of a series of *Buddleia* cultivars with well-branched habits, sterility, and cultivars in a range of colors. The new cultivar was created by cross-pollination wherein two parents were crossed which previously had been studied in the hope that they would contribute the desired characteristics. The female parent (i.e., the seed parent) was the 'TOBUD0802' variety (U.S. Plant Pat. No. 23,463). The male parent (i.e, the pollen parent) was an unnamed breeder seedling variety (not patented).

The parentage of the new variety can be summarized as follows:

'TOBUD0802' x unnamed breeder seedling

The new cultivar was discovered and selected as a single flowering plant from the progeny resulting from the above pollination during August 2014 in a controlled environment in Guadalupe, Calif. Selective study resulted in the identification of a single plant of the new variety.

It was found that the new variety of *Buddleia* plant of the present invention:

(a) forms deep purple colored flowers,
(b) displays dark green colored foliage,
(c) exhibits a moderately vigorous and upright growth habit, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'TOBUD0802' variety (i.e., the seed parent) displays magenta pink colored flowers, medium green colored foliage, and medium compact growth habit, while the new variety provides deep purple colored flowers, dark green colored foliage, and an upright growth habit. The unnamed breeding seedling male parent (i.e., the pollen parent) displays dark purple colored flowers and medium green-colored foliage, is very vigorous, and has a medium compact growth habit, while the new variety displays deep purple colored flowers and dark green colored foliage, is moderately vigorous, and has an upright growth habit.

The new variety can also be distinguished from other similar varieties that are commercially available. For instance, the new variety of the present invention can readily be distinguished from the 'Tobudpipur' variety (U.S. Plant Pat. No. 22,064), as the new cultivar displays a more upright growth habit than the 'Tobudpipur' variety and the flowers of the new variety are deeper purple colored than the flowers of the 'Tobudpipur' variety.

The new variety has been found to undergo asexual propagation by terminal stem cuttings. Asexual propagation by terminal stem cuttings in Guadalupe, Calif. since August 2014 has shown that the characteristics of the new variety are stable and are strictly transmissible by such asexual propagation from one generation to another. Accordingly, the new variety undergoes asexual propagation in a true-to-type manner.

The new variety has been named 'SRPbudroy'.

The new variety was first offered for sale on Jan. 9, 2019 at Baltimore, Md. by the inventor or by another who obtained the new variety directly or indirectly from the inventor.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'SRPbudroy' variety. The plants were grown in three-gallon pots for approximately four months outside at Cochranville, Pa. Plants were pinched once after transplant.

FIG. 1—illustrates a specimen of the plant displaying the overall growth and flowering habit—side view.

Figure 2:
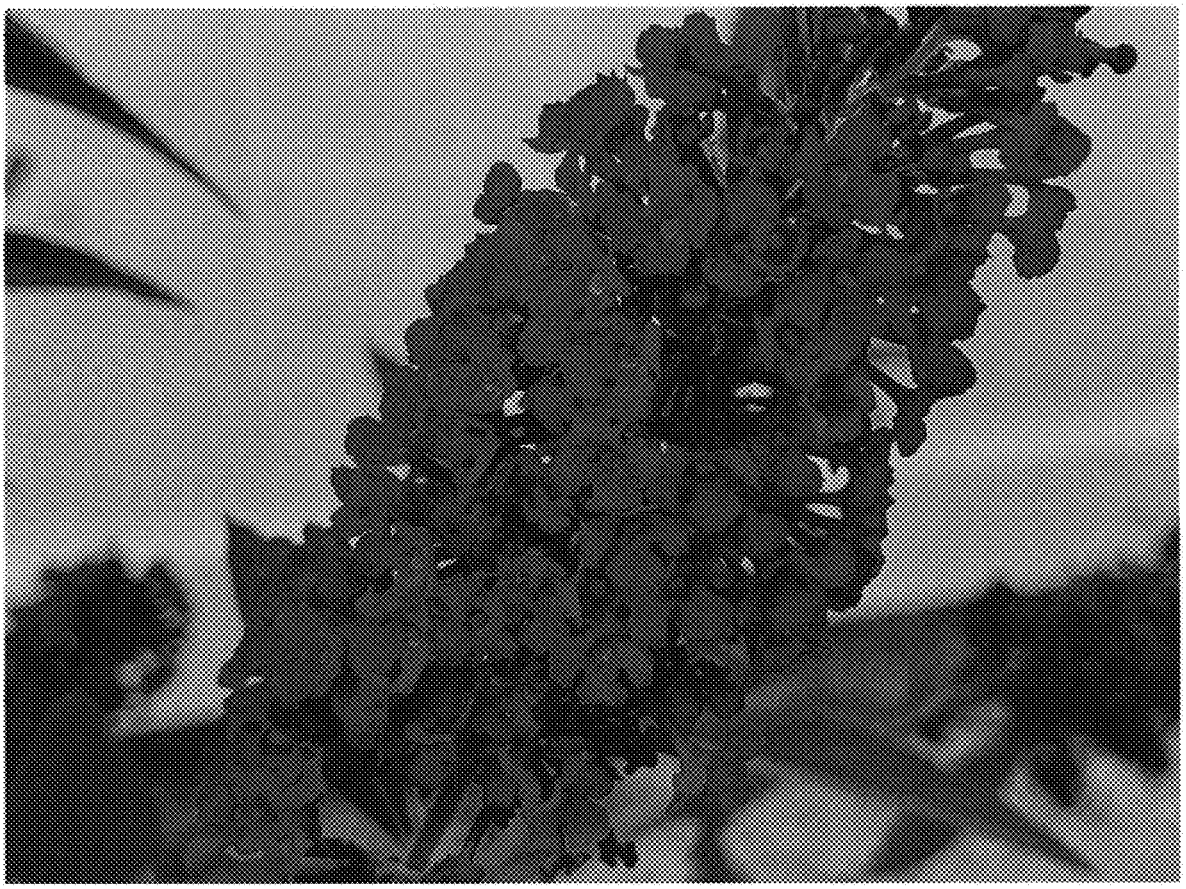

FIG. 2—illustrates a specimen of an inflorescence in the course of opening.

Figure 3:
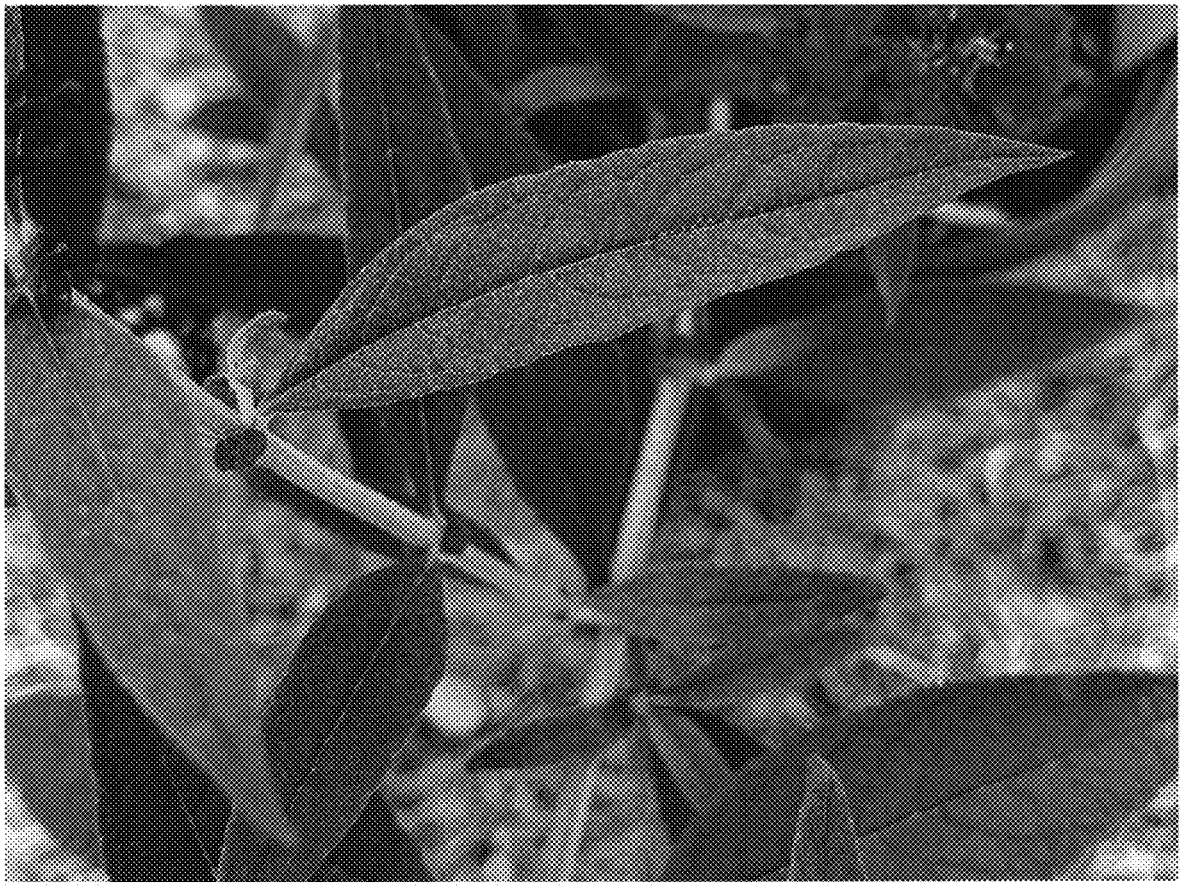

FIG. 3—illustrates specimens of leaves—plan view—obverse.

DETAILED BOTANICAL DESCRIPTION

The chart used in the identification of the colors is that of The Royal Horticultural Society (R.H.S. Colour Chart), 2015 edition, London, England. The terminology which precedes reference to the chart has been added to indicate the corresponding color in more common terms. The color values were determined in August 2019 under natural light conditions in Cochranville, Pa. The description is based on the observation of plants produced from cuttings from stock plants and grown in three-gallon containers for approximately four months in an outdoor nursery in Cochranville, Pa. Plants were pinched once after transplant.

Class: *Buddleia* Plant.

Common name: Butterfly bush.

Propagation:

*Type cutting*.—Terminal stem.

*Time to initiate roots*.—Approximately 10 to 14 days on average.

*Time to produce a rooted cutting*.—Approximately 21 to 25 days on average.

*Root description*.—Fibrous.

*Rooting habit*.—Freely branching.

Plant:

*Habit*.—Moderate growth vigor and upright.

*Commercial crop time*.—Approximately 2 months from a rooted cutting to finish in a 3 gallon container on average.

*Size*.—Approximately 50.0 cm in height from soil level to top of plant plane on average; and approximately 70.0 cm in width on average.

Branches:

*Branching habit*.—Freely branching, pinching enhances basal branching.

*Quantity of main branches per plant*.—Approximately 10 on average.

*Strength*.—Commonly strong, somewhat flexible and becomes woody with age.

*Size*.—Length: approximately 40.0 cm on average. — diameter approximately 5.0 mm on average. — length of central internode: approximately 6.0 cm on average.

*Texture*.—Viscid, densely glandular pubescent.

*Color*.—Young stems: commonly near Yellow-Green Group 146C with some coloring of near Brown Group 200B. — mature stems: commonly near Greyed-Orange Group 177C.

Foliage:

*Number of leaves*.—Approximately 30 per branch on average; and approximately 10 per branched lateral stem on average.

*Fragrance*.—None detected.

*Form*.—Simple.

*Arrangement*.—Opposite.

*Durability to stress*.—Moderate to high.

Leaves:

*Aspect*.—Primarily perpendicular to stem.

*Shape*.—General: lanceolate to oblanceolate. — margin: serrulate. — apex: acute. — base: attenuate.

*Venation*.—Pattern: pinnate, reticulate. — upper surface color: indistinguishable from the upper surface leaf color. — under surface color: commonly near Greyed-Green Group 192C.

*Size*.—Length of mature leaf: approximately 12.0 cm on average. — width of mature leaf: approximately 3.5 cm on average.

*Texture*.—Upper and lower surfaces: pubescent.

*Color*.—Upper surface of mature foliage: commonly between near Green Group 137A and 1378. — lower surface of mature foliage: commonly near Greyed-Green Group 192B.

*Petiole*.—Shape: rounded, slightly curved. — length: approximately 3.0 mm on average. — width: approximately 3.0 mm on average. — texture: densely pubescent with lanulose hairs. — color: commonly near Greyed-Green Group 192B.

Inflorescence:

*Quantity*.—Approximately 20 open inflorescences per plant on average, and approximately 500 flowers per inflorescence on average, opening from base to apex.

*Density of the flowers per inflorescence*.—Very dense.

*Type*.—Terminal panicles, each panicle having about 2 to 4 branches on average; and flowers persistent, facing upward and outward.

*Shape*.—Conical.

*Fragrance*.—Very faint.

*Depth or height*.—Approximately 15.0 cm on average.

*Width*.—Approximately 3.5 cm on average.

*Rachis*.—Strength: strong. — length: approximately 10.0 cm on average. — diameter: approximately 2.0 mm on average. — texture: pubescent with stellate hairs. — color: commonly near Yellow-Green Group 146B.

*Peduncle*.—Length: approximately 4.3 cm on average. — diameter: approximately 3.0 mm on average. — texture: slightly tomentose. — color: commonly near Greyed-Green Group 191B.

Flower:

*Type*.—Single, salverform.

*Bud just before opening*.—Shape: oblong. — length: approximately 6.0 mm on average. — diameter: approximately 1.0 mm on average. — texture: glabrous. — color of petals: commonly near Purple Group 77A.

*Corolla*.—Shape: rotate, commonly 4 petals arranged in a single whorl. — depth: approximately 1.0 cm on average. — width: approximately 8.0 mm on average. — corolla eye color: commonly near Orange Group 26A.

*Petals*.—Shape: rotund. — margin: erosulate. — apex: rounded. — length from throat: approximately 8.0 mm on average. — width: approximately 3.0 mm on average. — texture of upper and lower surfaces: glabrous. — color of upper and lower surfaces when first and fully open: commonly near Purple-Violet Group N81A.

*Corolla tube*.—Length: approximately 7.0 mm on average. — width: approximately 1.0 mm on average. — diameter of throat opening: approximately 1.0 mm on average. — inner surface: texture is lightly pubescent and color is commonly near Greyed-Orange Group N163B. — outer surface: texture is glabrous and color is commonly near Red-Purple Group 63B.

*Calyx*.—Shape: tubular. — length: approximately 3.0 mm on average. — diameter: approximately 1.0 mm on average.

*Sepals*.—Quantity per flower: commonly 4 on average, fused at base. — length: approximately 3.0 mm on average. — width: commonly less than 1.0 mm. — apex: acute. — margin of free portion: entire. — inner surface: — texture: glabrous. — color: commonly near Yellow-Green Group 144A. — outer surface: — texture: moderately pubescent. — color: commonly near Yellow-Green Group 144A.

*Pedicels*.—Strength: strong, flexible. — length: approximately 1.0 mm on average. — diameter: approximately 3.0 mm on average. — texture: densely pubescent with stellate hairs. — color: commonly near Yellow-Green Group 146C.

*Reproductive organs*.—Androecium. — Stamen: commonly 4 per flower, completely adnate to corolla. — filament: no noticeable filament observed to date. — anther: shape is lanceolate, length is approximately 1.0 mm on average, and color is commonly near Yellow Group 11C. — pollen: amount is moderate and coloration is commonly near Yellow Group 11C — gynoecium: — pistil: commonly 1 per flower, length is approximately 2.0 mm on average. — stigma: shape is cleft, two-parted, length is approximately 1.0 mm on average, and color is commonly near Yellow-Green Group 144A. — style: length is approximately 1.0 mm on average and coloration is commonly near Yellow-Green Group 145B, opaque. — ovary: length is approximately 1.5 mm on average and coloration is commonly near Yellow-Green Group 145A. — seed and fruit: none have been observed to date.

Development:

*Blooming*.—Freely flowering under outdoor growing conditions with substantially continuous blooming from late spring through mid-fall.

*Lastingness of individual flower*.—Approximately 5 days on average.

*Tolerance to disease and pest*.—Not observed to date.

*Hardiness zone*.—USDA zone 5.

The new 'SRPbudroy' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Buddleia* plant characterized by the following combination of characteristics:

(a) forms deep purple colored flowers, (b) displays dark green colored foliage, (c) exhibits a moderately vigorous and upright growth habit, and (d) is well suited for providing attractive ornamentation; substantially as herein shown and described.

* * * * *